United States Patent
Rosario-Melendez et al.

(10) Patent No.: US 12,090,217 B2
(45) Date of Patent: Sep. 17, 2024

(54) MAKEUP SETTING MOUSSE

(71) Applicant: L'OREAL, Paris (FR)

(72) Inventors: Roselin Rosario-Melendez, New York, NY (US); Stan Najmr, Rahway, NJ (US); Anne-Laure Bernard, New York, NY (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/944,928

(22) Filed: Jul. 31, 2020

(65) Prior Publication Data
US 2022/0031581 A1 Feb. 3, 2022

(51) Int. Cl.
| | |
|---|---|
| A61K 8/04 | (2006.01) |
| A61K 8/58 | (2006.01) |
| A61K 8/81 | (2006.01) |
| A61Q 1/06 | (2006.01) |
| A61Q 1/10 | (2006.01) |

(52) U.S. Cl.
CPC .............. *A61K 8/046* (2013.01); *A61K 8/585* (2013.01); *A61K 8/8152* (2013.01); *A61K 8/8158* (2013.01); *A61K 8/817* (2013.01); *A61Q 1/06* (2013.01); *A61Q 1/10* (2013.01); *A61K 2800/22* (2013.01); *A61K 2800/59* (2013.01); *A61K 2800/88* (2013.01)

(58) Field of Classification Search
None
See application file for complete search history.

(56) References Cited

U.S. PATENT DOCUMENTS

| | | |
|---|---|---|
| 5,155,199 A | 10/1992 | Hayashi |
| 6,367,484 B1 | 4/2002 | Ramin et al. |
| 6,464,111 B2 | 10/2002 | de LaForcade et al. |
| 8,252,296 B2 | 8/2012 | Chrisstoffels et al. |
| 8,597,670 B2 | 12/2013 | Colaco et al. |
| 9,884,017 B2 | 2/2018 | Tamarkin et al. |
| 10,258,547 B2 | 4/2019 | Kasai et al. |
| 2002/0027146 A1 | 3/2002 | Forcade et al. |
| 2004/0241126 A1 | 12/2004 | Sakuta |
| 2005/0031658 A1 | 2/2005 | Girier Dufournier et al. |

(Continued)

FOREIGN PATENT DOCUMENTS

| | | |
|---|---|---|
| DE | 60204011856 T2 | 2/2009 |
| EP | 1205175 B1 | 6/2006 |

(Continued)

OTHER PUBLICATIONS

Tish Jett. "Re-learning How to Blush" <http://tishjett.com/2012/02/re-learing-how-to-blush.html; Feb. 8, 2012> available Feb. 8, 2012; accessed Jun. 27, 2022 (Year: 2012).*

(Continued)

*Primary Examiner* — Nicole P Babson
(74) *Attorney, Agent, or Firm* — Womble Bond Dickinson (US) LLP

(57) ABSTRACT

A method of treating keratinous substrates, includes applying a makeup setting composition to a keratinous substrate having makeup formed thereon. The makeup setting composition includes a gas phase dispersed in a condensed phase. The condensed phase includes a water-soluble or water-dispersible film former. Kits and mousse-forming compositions are also provided.

19 Claims, 2 Drawing Sheets

(56) References Cited

U.S. PATENT DOCUMENTS

| | | |
|---|---|---|
| 2006/0188468 A1 | 8/2006 | Nguyen-Kim et al. |
| 2008/0020004 A1 | 1/2008 | Birkel et al. |
| 2008/0152681 A1 | 6/2008 | Brown et al. |
| 2012/0225832 A1 | 9/2012 | Foley et al. |
| 2014/0220090 A1 | 8/2014 | Del Rey Castriotto et al. |
| 2014/0234227 A1 | 8/2014 | Yelin et al. |
| 2016/0243021 A1 | 8/2016 | Collins et al. |
| 2016/0250137 A1 | 9/2016 | Noor et al. |
| 2017/0189320 A1 | 7/2017 | Chiou et al. |
| 2018/0092814 A1* | 4/2018 | Comeron ............ A61K 8/4993 |
| 2018/0369081 A1 | 12/2018 | Sakuma et al. |
| 2020/0113813 A1 | 4/2020 | Noe et al. |
| 2020/0246244 A1 | 8/2020 | Doan |

FOREIGN PATENT DOCUMENTS

| | | |
|---|---|---|
| EP | 1646663 B1 | 1/2007 |
| FR | 2715841 A1 | 8/1995 |
| FR | 2778559 A1 | 11/1999 |
| KR | 20210039669 A | 4/2021 |
| WO | 2005004821 A1 | 1/2005 |
| WO | 2005117813 A1 | 12/2005 |

OTHER PUBLICATIONS

Goussard et al. "Predicting the Surface Tension of Liquids: Comparison of Four Modeling Approaches and Application to Cosmetic Oils" Journal of Chemical Information and Modeling. vol. 57, n12, pp. 2985-2995 (Year: 2017).*

French Search Report and Written Opinion issued May 27, 2021 in French Patent Application No. 2008868, 7 pages.

Merriam Webster definition of mousse. Apr. 23, 2022.

Preliminary Search Report issued Sep. 23, 2021 in FR Patent Application No. 2012464, citing documents AW through AZ therein, 7 pages.

Database GNPD [Online] Mintel; Feb. 15, 2012, anonymous: "Nude Foam Make-Up", XP055838428, Database accession No. 1727807, 2 pages.

Database GNPD [Online] Mintel; Mar. 13, 2018, anonymous: "Air Brush Body Bronzer", XP055838455, Database accession No. 5522219, 3 pages.

Database GNPD [Online] Mintel; Aug. 31, 2012, anonymous: "Golden Shimmer Mist", XP055838466, Database accession No. 1858076, 3 pages.

Database GNPD [Online] Mintel; Aug. 16, 2017, anonymous: "Make-Up Finish", XP055838482, Database accession No. 5030431, 3 pages.

* cited by examiner

MAKEUP SETTING MOUSSE

TECHNICAL FIELD

The present disclosure relates to compositions for treating, caring for, and/or protecting keratinous substrates, as well as systems and kits comprising the compositions, and methods of using the compositions.

BACKGROUND

Color cosmetic products have been long used to improve the appearance of keratinous substrates and, in particular, skin. While long-wear or extended wear makeup formulas are in use, these products still have limitations, and a desire exists on behalf of some consumers to protect more substantially the appearance of a user's makeup after it has been applied.

One approach to providing such protection is to use a so-called makeup setting spray. These are products that sprayed as a fine mist onto the surface (generally the face) onto which the makeup had previously been applied. These products generally include a polymer carried in a water solution. It is presumed that the water evaporates leaving behind protective polymer.

However, the present inventors have recognized that merely misting a product onto the face may not form a durable, continuous protective film for a user's previously applied makeup. Accordingly, the present inventors have conceived of and surprisingly found that keratinous substrates having makeup formed thereon may be effectively treated with makeup setting compositions that in the form of a mousse or foam. This provides a pleasant user experience and is able to "set" the makeup that was previously applied.

SUMMARY

According to one aspect of the invention, a method of treating keratinous substrates, comprises applying a makeup setting composition to a keratinous substrate having makeup formed thereon wherein the makeup setting composition comprises a gas phase dispersed in a condensed phase, and wherein the condensed phase comprises a water-soluble or water-dispersible film former.

In certain exemplary embodiments the method further comprises shearing the makeup setting composition across the keratinous substrate to form a layer thereon.

In certain other exemplary embodiments, the shearing comprises manually contacting the makeup setting composition that has been applied to the keratinous substrate (e.g., the skin) to spread the makeup setting composition that has been applied to the keratinous substrate across said keratinous substrate.

In certain other exemplary embodiments, the makeup setting composition has a Surface Tension Value of less than about 63 mN/m and where propellant is removed from the composition.

In certain other exemplary embodiments, the makeup setting composition is produced by actuating a packaged makeup setting product that includes a mousse-forming composition such as one including the water-soluble or water-dispersible film former, water, and a propellant.

In certain other exemplary embodiments, the mousse-forming composition comprises from about 0.5% by weight to about 50% by weight of the water-soluble or water-dispersible film former.

According to another aspect of the invention, a mousse-forming composition is provided. The composition, includes propellant gas, water; and about 0.5% to about 50% by weight of a water-soluble or water-dispersible polymer. The mousse-forming composition has a Surface Tension Value of less than about 63 mN/m. The composition is substantially free of surfactant.

According to another aspect of the invention, a kit comprises a makeup application product. The kit further comprises a packaged makeup setting product. The packaged makeup setting product is configured to provide a produced makeup setting composition that comprises a gas phase dispersed in a condensed phase wherein the gas phase comprises the propellant, and wherein the condensed phase further comprises a water-soluble or water-dispersible film former. The packaged makeup setting product may include a mousse-forming composition that includes water and a propellant.

BRIEF DESCRIPTION OF THE DRAWINGS

The accompanying drawings, which are incorporated herein and constitute part of this specification, illustrate exemplary embodiments of the invention, and, together with the general description given above and the description provided herein, serve to explain features of the invention.

Figure 1:
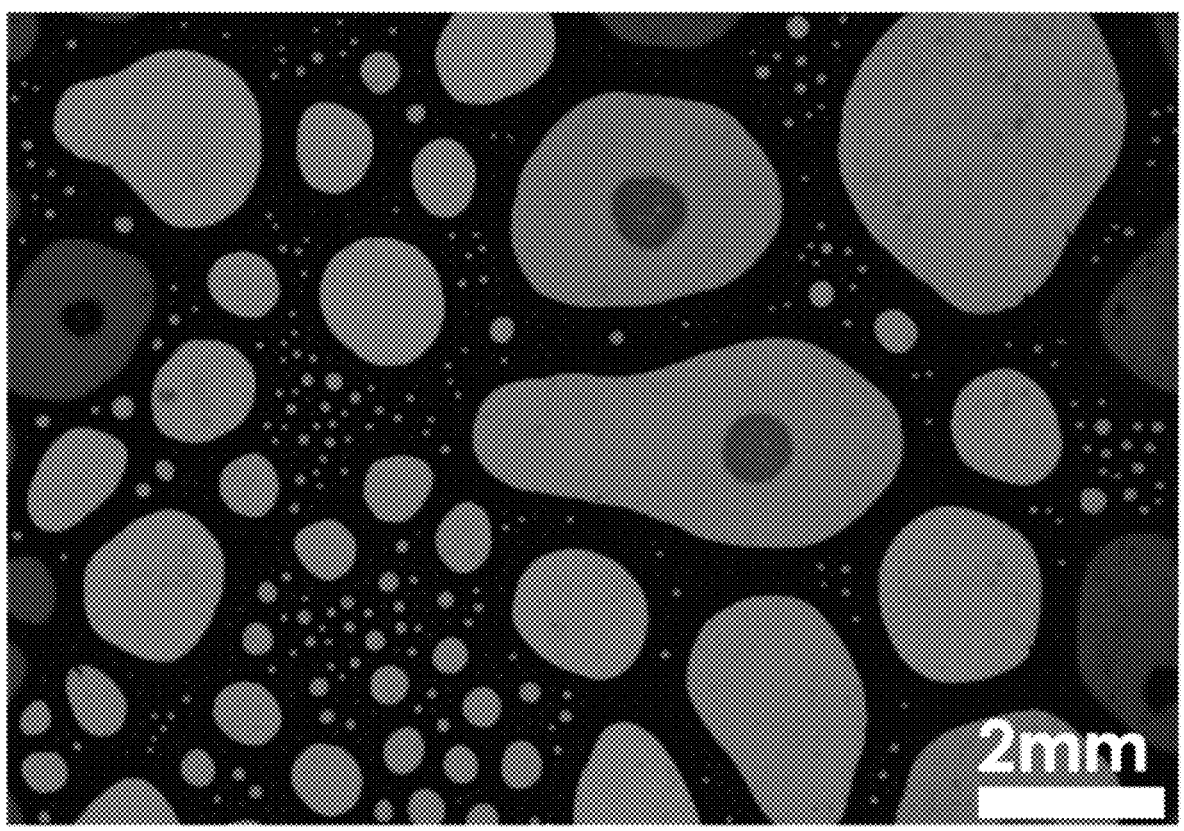
FIG. 1 is an image depicting the foam structure of a makeup setting composition according to embodiments of the invention described herein.

It is to be understood that the foregoing and following descriptions are exemplary and explanatory only, and are not intended to be restrictive of any subject matter claimed.

DETAILED DESCRIPTION

All percentages of ingredients herein are listed on an actives basis unless specifically stated otherwise. Further, all percentages of ingredients are in percent by weight unless specifically stated otherwise.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 15%, such as within 10%, of the indicated number. For example, about 10% means from 8.5% to 11.5%, such as between 9% and 11%.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated using test methods described herein.

"Substituted" as used herein, means comprising at least one substituent. Non-limiting examples of substituents include atoms, such as oxygen atoms and nitrogen atoms, as well as functional groups, such as amine groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphategroups, siloxane groups, and polysiloxane groups. The substituent(s) may be further substituted.

"Substantially free" as it is used herein means that while it is preferred that no amount of the specific component be present in the composition, it is possible to have very small amounts of it in the compositions of the invention provided that these amounts do not materially affect at least one, preferably most, of the advantageous properties of the conditioning compositions of the invention. In certain embodiments, substantially free means less than about 2% of the identified ingredient, such as less than about 1%, such as less than about 0.5%, such as less than about 0.1% of the ingredient. The term "anhydrous" means substantially free of water.

Numerical ranges are inclusive of endpoints and meant to include all combinations and sub-combinations. For example, from about 5%, 10% or 15% to about 20%, 50% or 60% means about 5% to about 20%, about 5% to about 50%, about 5% to about 60%, about 10% to about 20%, about 10% to about 50%, about 10% to about 60%, about 15% to about 20%, about 15% to about 50%, or about 15% to about 60%.

All concentrations in this specification are by weight unless otherwise specifically stated differently.

"Keratinous materials" includes materials containing keratin such as hair, skin, eyebrows, lips and nails. According to certain notable embodiments, the keratinous substrate is skin, such as skin of the face including around the cheeks, forehead, eyes, lips, or skin on other parts of the body.

"Volatile", as used herein, means having a flash point of less than about 100° C.

"Non-volatile", as used herein, means having a flash point of greater than about 100° C.

"Actives basis" as used herein means considering only the particular component of ingredient (e.g., in a composition) and ignoring other chemically unrelated components that may be also be present in the same raw material source of that particular component.

"Polymer" as used herein refers to a compound having molecules that comprise repeat units. In certain embodiments, polymer useful for embodiments described herein have a repeat unit comprising carbon and hydrogen, such as repeat units comprising carbon, hydrogen and optionally oxygen or nitrogen.

The compositions and methods of the present invention can comprise, consist of, or consist essentially of the essential elements and limitations of the invention described herein, as well as any additional or optional ingredients, components, or limitations described herein or otherwise useful.

The present disclosure relates to methods treating keratinous substrates using makeup setting compositions. The makeup setting compositions are in the form of a mousse or foam, i.e., they comprise a gas phase dispersed in a condensed phase.

By "mousse" or "foam" it is meant a system having two or more phases wherein a gas is dispersed in a condensed phase (liquid, gelled liquid, and/or solid) phase to form a foam structure. In certain embodiments the mousse or foam is a two phase system having a gas phase dispersed in a liquid or gelled liquid phase. The term mousse or foam is meant to exclude conventional sprays. By "conventional spray," it is meant a system in which tiny particles or droplets of liquid and/or solid that are suspended in a gas phase.

According to certain embodiments the mousse or foam, after being expelled from a container onto a user's palm will appear as an opaque mass with some visible thickness. Allowed to remain undisturbed on the user's palm, the opaque mass may retain its shape and appearance, without substantial visible change, for a period of time ranging from about two seconds to several hours or more. According to certain embodiments, the opaque mass may retain its shape and appearance for at least as long as about 10 seconds. According to certain other embodiments, the opaque mass may retain its shape and appearance for a period of time as least as long as one minute, such as least as long as two minutes, such as at least as long as five minutes, such as at least as long as ten minutes. During these periods of time a substantial portion of bubbles or cells of bubbles may remain ("remenant bubbles"). The remenant bubbles may be polydisperse or relatively monodisperse.

According to certain other embodiments, the mousse or foam may include at least some fraction of remenant bubbles of dispersed gas that range from about 0.25 mm to about 5 mm, such as from 0.5 mm to about 5 mm, such as from 1 mm to about 5 mm.

Figure 2:
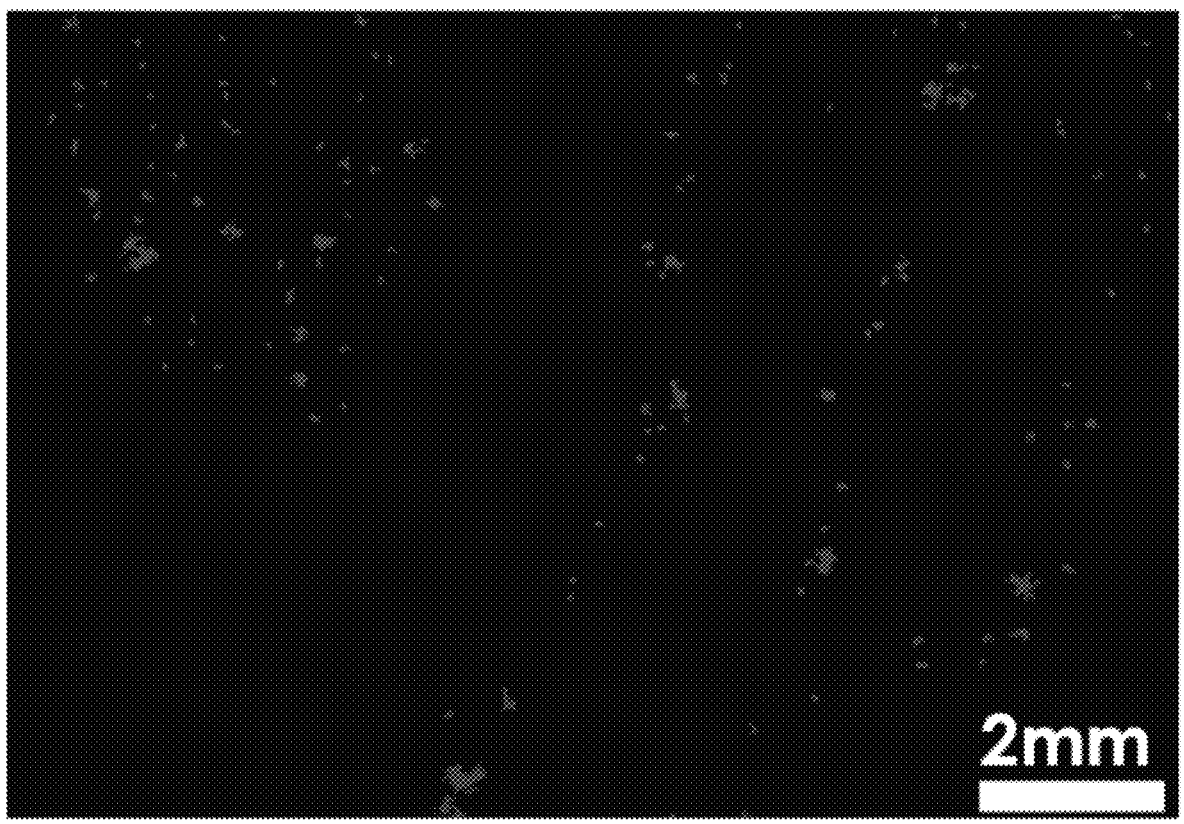
FIG. 2 is an image depicting the structure of a comparative composition.

The size of remenant bubbles may be determined using, for example, a DFA100 Foam Analyzer (KRUSS GmbH Wissenschaftliche Laborgerate). Approximately five grams of product may be dispensed in the foam analyzer's glass tube. An image can be acquired using the instrument's built-in camera one minute after dispensing the product. FIG. 1 depicts an image of a makeup setting composition consistent with embodiments of the invention described herein that was captured using this method, whereas FIG. 2 depicts an image captured of a conventional spray. Gray indicates bubbles of trapped gas whereas black indicates liquid or bubbles that are smaller in area than about 4838 $um^2$.

Packaged Makeup Setting Product

Embodiments of the present invention relate to packaged makeup setting products. By "packaged makeup setting product," it is meant a composition such as makeup setting composition that is contained within a primary package or container. This container may be made from any of various materials or constructions and is designed to protect and/or release the contents within. According to a first embodiment (herein after, "high pressure release"), the packaged makeup setting product has a container that is formed from a pressure resistant material such as metal and is designed to maintain contents under high pressure. It may include a pressure valve that, for example may be actuated by a user to release under pressure the contents thereof. In this embodiment, the foam or mousse may not exist inside the container, but may be created upon expulsion from the container. In a second embodiment (herein after, "manual foam pump") a non-aerosol packaging system creates a mousse or foam by mixing liquid contents in a foaming chamber and discharges the resultant composition through a mesh to create the mousse or foam.

According to third embodiment (herein after, "pre-existing mousse"), the package is not configured to maintain the contents under high pressure, and the user can expel the contents by for example scooping, squeezing the container, extruding, etc. In this embodiment, the foam or mousse may exist inside the container even prior to removal from the container.

Contents of Packaged Makeup Setting Product/Mousse-Forming Composition

According to the high pressure release embodiment described above, the packaged makeup setting product generally has various mechanical contents such as a release valve or other optional mechanical packaging contents (e.g., bag-on-valve) as well as flowable contents configured to be released under pressure. In this embodiment, the flowable contents of the packaged makeup setting product flow from the container upon actuation by a user. A portion or the substantial entirety of these may be released and/or incorporate into a resulting makeup setting composition to be applied to a keratinous substrate.

In this embodiment, the flowable contents of the packaged makeup setting product may include propellant described in more detail below as well as other flowable contents (e.g., a "concentrate") that are mixed with the propellant.

In the high pressure release embodiment, other flowable contents may include any of various ingredients designed to be incorporated into the makeup setting composition to be applied to the keratinous substrate. These are described in detail in this specification. In another embodiment of the high pressure release embodiment, propellant is employed to release the contents of the of the packaged makeup setting product, however the propellant is isolated from the contents using a bag-on-valve configuration.

In certain embodiments of the high pressure release embodiment as well as in the manual foam pump embodiment, the proportions and/or nature of the contents inside the container may be transformed upon exiting the container. The transformation may include, for example, a mousse being created after expulsion from the container through the mixing of propellant with the other flowable contents. The transformation may include the creation of foam via manual pumping of contents in the package through mesh. The transformation may also include, for example, the loss of some propellant escaping and not be incorporated into the mousse.

In the pre-existing mousse embodiment described above, the contents of the packaged makeup setting product may be nearly identical or identical to the makeup setting composition, as no substantial transformation may occur in the contents before and after removal from the container.

The combination of optional propellant and other flowable contents (e.g., a concentrate for use in a high pressure release system) in the packaged makeup setting product collectively form a mousse-forming composition that forms a mousse when expelled, produced or otherwise removed from the container.

According to certain embodiments of the invention the packaged makeup setting product is configured to create a makeup setting composition that has good foaming properties. In particular, the packaged makeup setting products of the present invention may include a mousse-forming composition that produces a slowly dissipating foam.

In order to assess the speed of foam dissipation, the following Foam Collapse Rate Test may be used. Foam collapse rate can be determined using, for example, a DFA100FSM Foam Analyzer (KRUSS GmbH Wissenschaftliche Laborgerate). A product to be tested is dispensed into the bottom of the instrument's glass tube, at which point acquisition of the foam's volume begins. The volume is recorded at two time points: when the foam has fully developed (i.e., when the foam reached maximum volume), and when the foam has collapsed (i.e. when the foam reaches its minimum volume after being dispensed). The Foam Collapse Rate is calculated as that change in volume over the change in time.

According to certain embodiments of the invention, the Foam Collapse Rate of the mousse-forming composition may be less than about than about 0.7 ml/s such as less than about 0.3 ml/s, such as less than about 0.05 ml/s, such as less than about 0.025 ml/s.

According to certain embodiments of the invention, the mousse-forming composition includes water, propellant, and water-soluble or dispersible polymer. The water-soluble or dispersible polymer may be present in the mousse-forming composition in a concentration from about 0.5% to about 50% by weight. Furthermore, the water-soluble or water-dispersible polymer may have a Surface Tension Value (as described herein) of less than about 63 mN/m. Furthermore, the mousse-forming composition may be substantially free of surfactant.

Makeup Setting Composition

After the contents such as the mousse-forming composition are expelled from or otherwise removed from the packaged makeup setting product, this produces (in the case of high pressure release) or delivers the resulting makeup setting composition that is ready to be applied to keratinous material having makeup formed thereon.

Water-Soluble or Water-Dispersible Film Former

The makeup setting compositions and mousse-forming compositions of the present invention generally include a water-soluble or water-dispersible film former. One of ordinary skill in the art will readily appreciate the term "film-former" or "film-forming agent" as used herein means a material such as a polymer or resin that leaves a film (e.g., a continuous film) on the substrate to which it is applied, for example, after a solvent accompanying the film former has evaporated, absorbed into and/or dissipated on or from the substrate. According to certain embodiments, the film former when tested according to the following drawdown test forms a conformal coating and/or can picked up or scraped off with a razorblade to be removed as a free standing film. Five to ten grams of material is placed on the center of a Leneta card stock (Black and White Opacity card Chart 2812 available from BYK Additives and Instruments of Geretsried, Germany) and using a 3 mil Drawdown Birdbar (also from Byk), the material is spread across the sheet (8 in by 3 in) and allowed to dry overnight. Film-formers that are cosmetically or dermatologically acceptable may be utilized in the present invention. As used herein, "cosmetically acceptable" or "dermatologically acceptable" is intended to mean that a composition is suitable for use in contact with human tissues such as keratinous materials and mucous membranes without undue toxicity, incompatibility, instability, and/or allergic response.

Additionally, one skilled in the art will appreciate that "water-soluble" refers to ingredients that completely solubilize in deionzed water, such as in a concentration of 1% by weight, and remain solubilized at room temperature and atmospheric pressure for a year or more or indefinitely. Similarly, "water-dispersible" refers to ingredients that although they do not completely solubilize in deionized water as a water-soluble ingredient would, such ingredients do not visibly phase separate at 1% by weight with the water and can in such state for extended time periods as described above. Water-dispersible ingredients may require small concentrations (e.g., one-tenth or less, such as one-twentieth or less of the concentration of ingredient to be dispersed) of dispersant to remain dispersed. Accordingly, "water-soluble or water-dispersible polymers" are generally polymers that do not visibly phase separate under the conditions described above when placed in deionized water at 1% by weight either alone or with small quantities of dispersant.

Suitable types of film-formers include anionic, non-ionic, cationic, amphoteric, or zwitterionic polymers.

Suitable anionic polymers can be a homo- or copolymer with acid group-containing monomer units derived from natural or synthetic sources, which, if necessary, can be polymerized with comonomers that contain no acid groups. Among the acid groups that can be considered are sulfonic acid, phosphoric acid and carboxylic acid groups, of which the carboxylic acid groups are preferred. Suitable acid group-containing monomers are, for example, acrylic acid, methacrylic acid, crotonic acid, maleic acid, and maleic anhydride, maleic acid monoesters, especially the C-1 to C-7 alkyl monoesters of maleic acid, as well as aldehydocarboxylic acids or ketocarboxylic acids. Comonomers that are not substituted with acid groups are, for example, acrylamide, methacrylamide, alkyl- and dialkylacrylamide, alkyl- and dialkylmethacrylamide, alkyl acrylate, alkyl methacrylate, vinylcaprolactone, vinylpyrrolidone, vinyl ester, vinyl alcohol, propylene glycol or ethylene glycol, amine-substituted vinyl monomers such as, for example, dialkylaminoalkyl acrylate, dialkylaminoalkyl methacrylate, monoalkylaminoalkyl acrylate and monoalkylaminoalkyl methacrylate, wherein the alkyl groups of these monomers are for example C-1 to C-7 alkyl groups.

Anionic polymers can be partially or completely neutralized with a basic neutralizing agent. A preferred degree of neutralization is from about 50% to about 100%, and from about 70% to about 100% is especially preferred. An organic or inorganic base can be used as the neutralizing agent. Particular examples of bases are amino alkanols such as, for example, aminomethylpropanol (AMP), triethanolamine or monoethanolamine, and also ammonia, NaOH, and KOH among others.

Illustrative anionic polymers are acrylic polymers such as AMP-acrylates/allyl methacrylate available as FIXATE G-100 from Noveon.

Suitable nonionic film formers include homo- or copolymers that are formed from at least one of the following monomers: vinylpyrrolidone, vinylcaprolactam, vinyl esters such as, for example, vinyl acetate, vinyl alcohol, acrylamide, methacrylamide, alkyl- and dialkylacrylamide, alkyl- and dialkylmethacrylamide, alkyl acrylate, alkyl methacrylate, propylene glycol or ethylene glycol, where the alkyl groups in these monomers are for example C-1 to C-7 alkyl groups. Suitable homopolymers are, for example, those of vinylcaprolactam, vinylpyrrolidone or N-vinylformamide. Further suitable synthetic, film-forming, nonionic, hair-setting polymers are, for example, copolymerides from vinylpyrrolidone and vinyl acetate, terpolymers from vinylpyrrolidone, vinyl acetate and vinyl propionate, polyacrylamides; polyvinyl alcohols as well as polyethylene glycol/polypropylene glycol copolymers. Suitable natural, film-forming polymers are, for example, cellulose derivatives, e.g., hydroxyalkylcellulose.

For example, the nonionic film former may be a polyvinylpyrrolidone, polyvinylcaprolactam, vinylpyrrolidone/vinyl acetate copolymers, polyvinyl alcohol, isobutylene/ethylmaleimide/hydroxyethylmaleimide copolymer; copolymers from vinylpyrrolidone, vinyl acetate and vinyl propionate. In one notable embodiment, the nonionic film former is a polyvinylcaprolactam, such as is commercially available from BASF as LUVISKOL PLUS.

Suitable cationic film formers include cationic polymers, especially those with primary, secondary, tertiary, or quaternary amino groups. Suitable cationic polymers preferably contain quaternary amino groups. Cationic polymers can be homo- or copolymers, where the quaternary nitrogen groups are contained either in the polymer chain or preferably as substituents on one or more of the monomers. The ammonium group-containing monomers can be copolymerized with non-cationic monomers. Suitable cationic monomer are unsaturated compounds that can undergo radical polymerization, which bear at least one cationic group, especially ammonium-substituted vinyl monomers such as, for example, trialkylmethacryloxyalkylammonium, trialkylacryloxyalkylammonium, dialkyldiallylammonium and quaternary vinylammonium monomers with cyclic, cationic nitrogen-containing groups such as pyridinium, imidazolium or quaternary pyrrolidones, e.g., alkylvinylimidazolium, alkylvinylpyridinium, or alkylvinylpyrrolidone salts. The alkyl groups of these monomers are preferably lower alkyl groups such, as for example, C-1 to C-7 alkyl groups.

For example, cationic film-forming polymers may include quaternized cellulose ethers such as Polyquaternium 10 (hydroxyethylcellulose hydroxypropyl trimethylammonium chloride ether) Polyquaternium 4 (hydroxyethylcellulose, dimethyldiallyl ammonium chloride copolymer), quaternized vinyl pyrrolidone/alkylaminoacrylate or methacrylate copolymers such as dimethyl sulfate salt; methylvinylimidazolium vinylpyrrolidone; N-methacryloyl ethyl-N,N'-dimethyl ammonium gamma-N-methyl carboxy betaine butyl methacrylate copolymer, and mixtures thereof.

Suitable zwitterionic or amphoteric film former include polymers such as: copolymers formed from alkylacrylamide, alkylaminoalkyl methacrylate, and two or more monomers from acrylic acid and methacrylic acid as well as, if necessary, their esters, especially copolymers from octylacrylamide, acrylic acid, butylaminoethyl methacrylate, methyl methacrylate and hydroxypropyl methacrylate (INCI designation: Octylacrylamide/Acrylate/Butylaminoethyl Methacrylate Copolymer; e,g, AMPHOMER from Nouryon); copolymers, that are formed from at least one of a first type of monomer that possesses quaternary amino groups and at least one of a second type of monomer that possesses acid groups; copolymers from fatty alcohol acrylates, alkylamine oxide methacrylate and at least one monomer selected from acrylic acid and methacrylic acid as well as, if necessary, acrylic acid esters and methacrylic acid esters, especially copolymers from lauryl acrylate, stearyl acrylate, ethylamine oxide methacrylate and at least one monomer selected from acrylic acid and methacrylic acid as well as, if necessary, their esters; copolymers from methacryloyl ethyl betaine and at least one monomer selected from methacrylic acid and methacrylic acid esters; copolymers from acrylic acid, methyl acrylate and methacrylamidopropyltrimethylammonium chloride (INCI designation: Polyquaternium-47); copolymers from acrylamidopropyltrimethylammonium chloride and acrylates or copolymers from acrylamide, acrylamidopropyltrimethylammonium chloride, 2-amidopropylacrylamide sulfonate and dimethylaminopropylamine (INCI designation: Polyquatemium-43); oligomers or polymers, producible from quaternary crotonoylbetaines or quaternary crotonoylbetaine esters.

The concentration of the water-soluble or water-dispersible film-former in the mousse-forming composition or in the makeup setting composition may be any suitable concentration for forming a continuous film on the keratinous substrate. According to certain embodiments, the concentration ranges from about 0.5% to about 50%. According to certain other embodiments, the concentration by weight ranges from about 0.2%, 0.5%, 0.75, or 1% to about 1%, 3%, 5%, 10%, or 20%. Similarly, the concentration by weight of the water-soluble or water-dispersible film-former may fall within these ranges when incorporated into the mousse-forming composition or makeup setting composition.

Water

Mousse-forming compositions used in packaged make up setting products as well as makeup setting compositions useful in the present invention include water to serve as a vehicle in which to dissolve or disperse the water-dispersible or water-soluble film-former. The concentration of water in the mousse-forming composition may range, for example, from about 10% to about 99%, such as from about 15%, 25%, 40%, or 50% to about 50%, 70%, 85%, 90%, 95% or 99% by weight. According to certain embodiments, the above concentrations are calculated relative to the entire mousse-forming composition except for propellant. In this embodiment, mass/concentration of propellant is not considered in the calculation. Similarly, the concentration by weight of the water may fall within these above ranges when incorporated into the makeup setting composition.

Propellant

As discussed above, in certain embodiments, a propellant is included in the mousse-forming composition in order to provide a source of gas to aid in expelling the contents of the packaged makeup setting product and/or to act as a source of gas to be incorporated into the makeup setting composition. The propellant may partially or completely incorporate into the makeup setting composition.

Propellant gas can be any liquefiable gas conventionally suitable for pressurized containers. Preferably the density of the propellant or mixture thereof is less than 1. Examples of materials that are suitable for use as propellants are volatile liquefied propellant gases, such as, for example, dimethyl ether (DME) and/or linear or branched-chain hydrocarbons with two to five carbon atoms, such as, for example, ethane, propane, butane, isobutane, isobutene, pentane and tetrafluoropropene, used singly or in combination. According to certain other embodiments, such as when using bag-on-valve configuration, compressed air may be used as a propellant.

The concentration by weight of propellant in the mousse-forming composition may range from, for example, 1% to about 25%, such as from about 2%, 4% or 5% to about 10%, 15%, 20% or 30% by weight. Similarly, the concentration by weight of the propellant may fall within these ranges when incorporated into the makeup setting composition.

Other Components

Mousse-forming compositions and makeup setting compositions according to the disclosure may optionally further include or exclude various ingredients useful for providing makeup setting performance and/or foam creation, foam stability, and the like.

In certain embodiments, mousse-forming compositions and makeup setting compositions of the present invention are substantially free of polymers that are neither water-soluble nor water-dispersible. Polymers that are neither water-soluble nor water-dispersible generally do not meet the definition of water-soluble or water-dispersible as described above. Such polymers are, in certain embodiments soluble in non-polar or fatty compounds such as isododecane and/or in silicone compounds such as polydimethylsiloxane.

The inventors have found that in certain embodiments, the presence of polymers that are neither water-soluble nor water-dispersible tend to create one or more problems such as reducing foam performance, disturbing/removing makeup during application, and/or causing the makeup to become less transfer resistant.

In certain embodiments, mousse-forming compositions and makeup setting compositions may include surfactants or emulsifiers, such as in order to enhance foam. Suitable surfactants and emulsifiers include any of various anionic, nonionic, cationic, or amphoteric surfactants, and mixtures thereof. According to certain embodiments, the term "surfactant" means a compound having at least one hydrophilic portion and at least one hydrophobic portion and wherein when it is added to deionized water in a concentration of 0.25% is capable of reducing surface tension of water to less than about 60 mN/m, such as less than about 50 mN/m. In certain other embodiments, the definition of surfactant as used herein is meant to exclude polymeric compounds.

The term "cationic surfactant" means a surfactant comprising, as ionic or ionizable groups, only cationic groups. Non-limiting examples of cationic surfactants that may be used include polyoxyalkylenated primary, secondary, or tertiary fatty amine salts, quaternary ammonium salts, and mixtures thereof. Mention may be made of tetraalkylammonium halides, such as chlorides, for example dialkyldimethylammonium or alkyltrimethylammonium chlorides in which the alkyl group comprises from 12 to 22 carbon atoms, such as from 14 to 20 carbon atoms. By way of example, behenyltrimethylammonium chloride (behentrimonium chloride), distearyldimethylammonium chloride, cetyltrimethylammonium chloride (cetrimonium chloride), or benzyldimethylstearylammonium chloride may be chosen.

In certain embodiments according to the disclosure, the compositions may include one or more anionic surfactants. The term "anionic surfactant" means a surfactant comprising, as ionic or ionizable groups, only anionic groups. These anionic groups may optionally be chosen from the groups $CO_2H$, $CO_2^-$, $SO_3H$, $SO_3^-$, $OSO_3H$, $OSO_3^-O_2PO_2H$, $O_2PO_2H$ and $O_2PO_2^{2-}$.

Non-limiting examples of anionic surfactants include alkyl sulfates, alkyl ether sulfates, acyl isethionates, acyl glycinates, acyl taurates, acyl amino acids, acyl sarcosinates, sulfosuccinates, sulfonates, and a mixture thereof, wherein the alkyl and acyl groups of all these compounds comprise from 6 to 24 carbon atoms. In some cases, anionic sulfate surfactants may be excluded from the one or more anionic surfactants. In such cases, the one or more anionic surfactants may be selected from the group consisting of acyl isethionates, acyl glycinates, acyl taurates, acyl amino acids, acyl sarcosinates, sulfosuccinates, sulfonates, and mixtures thereof, wherein the alkyl and acyl groups of all these compounds comprise from 6 to 24 carbon atoms.

Useful non-ionic surfactant(s) can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and a mixture thereof.

Non-limiting examples of amphoteric surfactants useful in the compositions include, for example, optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of (C8-C20)alkylbetaines, sulfobetaines, (C8-C20)alkylsulfobetaines, (C8-C20)alkylamido(C1-C6)alkylbetaines, such as cocamidopropylbetaine, and (C8-C20)alkylamido(C1-C6)alkylsulfobetaines, and mixtures thereof. For example, mention may be made of compounds classified under the INCI names sodium cocoamphoacetate, sodium lauroamphoacetate, sodium caproamphoacetate and sodium capryloamphoacetate.

According to certain embodiments, the concentration of surfactants in the mousse-forming compositions and/or makeup setting compositions useful in the present invention may be selected so as not to interfere with or detract from the foaming of the product and/or the performance (e.g., make up disruption during application or subsequent makeup transfer resistance). If present, the total amount of the one or more surfactants can range from about 0.001% to about 10% by weight, relative to the total weight of the composition, including all ranges and subranges therebetween. In certain embodiments, such as, for example, when the surface tension of the mousse-forming composition at the liquid air interface (using methods described below) is less than about 63 mN/m, the packaged makeup setting product and/or the makeup setting composition is substantially free of surfactants and emulsifiers.

Mousse-forming compositions and makeup setting compositions useful in embodiments provided herein may optionally include other components suitable for use in cosmetic compositions. Such components may include, but are not limited to, colorants such as dyes/pigments, thickening agents, humectants and moisturizing agents, fatty substances, fillers, antioxidants, sequestrants, fragrances, buffers, dispersants, plant extracts, volatile or non-volatile solvents, preserving agents, sunscreen agents, vitamins, pH adjusting agents. In certain embodiments, the makeup setting products and makeup setting compositions are substantially free of fatty substances, such as oils and waxes. One skilled in the art will recognize that "fatty substances" generally refer to water-incompatible and/or hydrophobic substances that don't meet the definition herein of a surfactant. "Oil" means any non-aqueous medium which is liquid at ambient temperature (25° C.) and atmospheric pressure (760 mm Hg). A "wax" refers to lipophilic fatty compounds that is solid at ambient temperature (25° C.) and changes from the solid to the liquid state reversibly, having a melting temperature of more than 30° C. and, for example, more than 45° C., which can be as high as 150° C., a hardness of more than 0.5 MPa at ambient temperature, and an anisotropic crystalline organization in the solid state.

Optional other components may be present in an amount ranging from about 0.0001% to about 15% by weight, relative to the total weight of the compositions.

Mousse-forming compositions and makeup setting compositions useful according to the present invention may have a pH in a range from about 3.5 to about. 9.5 such as from about 4 to about 8.

Mousse-forming compositions and makeup setting compositions useful according to the present invention, according to certain embodiments have a surface tension when measured at the air liquid interface at a time period of five minutes (Surface Tension Value) that is less than about of less than about 63 mN/m, wherein the surface tension is at about five minutes from the time of dispensing and with propellant removed from the composition. According to other embodiments the Surface Tension Value is less than about 60 mN/m, such as less than about 44 mN/m, such as less than about 42 mN/m.

Surface tension measurements to calculate Surface Tension Value may be performed, for example, using Pendant Drop Method at room temperature with an Attension Theta Optical Tensiometer (Biolin Scientific). The tensiometer can be equipped with an Automatic XYZ Sample Stage (T330) and an Automatic Single Liquid Dispenser (C201). The test is performed according to the equipment manufacturer's instructions. Propellant should be allowed to volatilize from the test samples so as not to interfere with the reading. The instrument is calibrated using a metal ball (NIST No. 821/263669-00) and the samples introduced using a 1 mL glass syringe. The syringe is rinsed with ethanol and deionized (DI) water prior to each sample. Before starting the measurements any droplets on the needle are wiped off using Kimwipes™ disposable wipes. Standardization tests with DI water (70-72 mN/m surface tension) are performed before each sample. Each composition is tested in triplicate by analyzing a 54 drop automatically dispensed at a rate of 2 µL/s. Data is collected at a rate of 6.0 FPS (frames per second) and analyzed using One Attension Software. The average and standard deviation for each sample is then calculated using the moving averages. Surface Tension Value (mN/m) is reported as the reading at 5 minutes.

Methods of Making and Using

The packaged makeup setting product is prepared by combining the ingredients, including the water and water-soluble or water-dispersible film-former, in a vessel with optional heat, while mixing until all solids are dissolved or dispersed, providing an aqueous phase. An optional oil phase, if used, can be prepared and combined with the aqueous phase such as to form an emulsion. Gelling agents can be included to gel one or more of the phases, if appropriate. The resulting compositions may be filled into a dispensing can or other container, delimiting at least one compartment which comprises the composition optionally with a suitable amount of propellant either mixed with the composition or into a separate bag (bag-on-valve embodiment) for discharge of the contents, optionally along with propellant. The container may be used in combination with an applicator comprising at least one application component configured in order to apply the composition to keratinous substances.

The water-soluble or dispersible materials may be mixed with water to form a "concentrate". This concentrate, in an appropriate amount, may be placed into an aerosol container. The container may then be then fitted with a valve, subjected to a vacuum to rid the container of air and sealed with the valve "crimped" in place. Propellant fluid and the propellant may then be filled into the container through the valve to provide the mousse-forming composition.

In other embodiments, the ingredients may be combined and sheared under high speed mixing without propellant, in order to create a mousse that is shelf-stable under atmospheric pressure. This stable mousse may be packaged as a ready to use mousse or foam.

In another embodiment (such as in the manual foam pump embodiment) the container is equipped with a hand pump apparatus so that the contents in the package move through mesh in order to aerate the contents and form a foam or mousse at an exit nozzle.

Systems and Kits

Embodiments of the present disclosure further provide systems and kits including any of the packaged makeup setting described herein. In various embodiments, a kit includes a makeup application product. The makeup application product is a packaged product that includes makeup to be applied to a keratinous substrate such as the skin. The makeup application product may be selected from one or more of products including colorants. Examples any of various products in liquid or powder form, include primer, bronzer, foundation, concealer, highlighter, blush, eyeshadow, eyeliner, mascara, lipstick, lip liner, lip gloss, and the like, and combinations thereof.

The kit further includes a packaged makeup setting product that includes water and a propellant. In certain embodiments the water and a propellant are mixed together along with other ingredients such as water-soluble or water-dispersible film-formers to form a mouse-forming composition within a container of the packaged makeup setting product. The packaged makeup setting product is configured to provide a produced makeup setting composition that comprises a gas phase dispersed in a condensed phase, wherein the gas phase comprises the propellant, and wherein the condensed phase further comprises a water-soluble or water-dispersible film former. The makeup setting composition may be "produced" by actuating for example a nozzle or pump so that the makeup setting composition forms a mousse in situ, or it may be produced by squeezing, extruding or otherwise removing a pre-formed mousse.

Methods of Using Make Up Setting Compositions

Methods according to the disclosure comprise treating, caring for, or conditioning keratin substrates with the compositions described herein. The methods generally comprise applying any of the disclosed makeup setting compositions to the keratinous substrates, e.g. to the skin. In certain embodiments, the keratinous substrate is the skin of the face including around the neck, cheeks, forehead, eyes, lips, and the like. In other embodiments, the keratinous substrate is skin around other areas of the body such as legs, arms, and the like.

According to certain embodiments, the method includes shearing the makeup setting composition across the keratinous substrate to form a layer thereon. The shearing may include manually contacting the makeup setting composition that has been applied to the keratinous substrate to spread the makeup setting composition that has been applied to the keratinous substrate across said keratinous substrate.

The shearing may be performed by spreading the mousse across the substrate using the fingers or an applicator. The applicator may be attached to the packaged makeup setting product or it may be a stand-alone device designed to minimize pressure applied to the substrate.

According to certain embodiments the method includes releasing a mousse-forming composition from the packaged makeup setting product to form a makeup setting composition. The makeup setting composition is then applied to the keratinous substrate as described above.

EXAMPLES

The following examples are intended to be non-limiting and explanatory in nature only. In the Examples, amounts are expressed in percentage by weight (wt %) of active materials.

Example I—Foam Performance, Makeup Removal During Application and Makeup Non Transference Six samples were prepared by combining water, isobutene propellant, and for certain examples a water-soluble or water-dispersible polymer or a water-insoluble polymer. The ingredients and concentrations are shown in Table 1.

TABLE 1

| Ref. | Water | Isobutane | Water-soluble or Water-dispersible polymer | Non water-soluble/ dispersible polymer |
|------|-------|-----------|-------------------------------------------|----------------------------------------|
| C1 | 94% | 6% | — | — |
| C2 | 94% | 6% | — | 5% Trimethylsiloxysilicate[1] |
| C3 | 94% | 6% | — | 5% Acrylates/ Polytrimethylsiloxymethacrylate Copolymer[2] |
| E1 | 89% | 6% | 5% Octylacrylamide/ acrylates/butylaminoethyl methacrylate[3] | — |
| E2 | 89% | 6% | 5% AMP-acrylates/allyl methacrylate[4] | — |
| E3 | 89% | 6% | 5% polyvinylcaprolactam[5] | |

[1]SILSOFT 74 from Momentive
[2]DOWSIL FA 4002 from Dow Chemical
[3]AMPHOMER LV-71 from Nouryon
[4]FIXATE G-100PR from Lubrizol
[5]LUVISOL PLUS from BASF Concentrate compositions were prepared by adding 2.5% active polymer by mass in deionized water. Specifically, water was charged to a vessel and mixed on a Silverson homogenizer operating at 2000 rpm, and polymer was added slowly until fully incorporated. For reference E1, aminomethyl propanol was added at a 1:5 ratio to the polymer to neutralize the solution and incorporate the polymer.

Then, 47 mL of each of the prepared concentrates above were filled into 100 mL Valspar 32S39MD Dot 2Q aluminum cans. A P10399 mousse valve from Precision Valve Corporation was cramped onto the opening of the can to create a seal. Three (3) g of propellant (isobutane) was then injected into the can, making the ratio of propellant to concentrate 6:94. The product was then placed in a water bath at 55° C. for 1 hour to ensure no leakage of propellant. The product was then removed from the bath and kept at room temperature undisturbed overnight. The foam was dispensed from the product using a Mars actuator from Precision Valve Corporation.

The test compositions were evaluated using three separate testing protocols.

The first test for Foam Quality was performed by dispensing approximately 1 mL of product onto a weigh tray, inspecting visually, and ranking. "High" indicates a foam that develops significant volume after being dispensed, low-to-no breakage, and good stiffness. In general, High foams will be stable beyond 10 minutes of being dispensed. "Moderate" indicates a foam that developed some volume, some breakage, and/or apparent pooling of formula around the foam. In general, Moderate foams will collapse within 10 minutes of being dispensed. "Low" indicates a foam that showed low-to-no foam development and quick pooling of formula. In general, Low foams will collapse within 1 min of being dispensed.

The second test, for Makeup Removal During Application was performed by placing a tape template on the skin of the forearm, leaving approximately a 1.5×1.5 mm square of skin bare. A liquid foundation (L'OREALTrue Match) was applied over the template. The foundation was allowed to dry for 10 minutes. Then, the test material was applied to the surface of the foundation using a finger, and the finger is assessed visual after application. "High" indicates significant transfer of makeup onto the finger. "Moderate" indicates some transfer of makeup onto the finger. "Low," the most desirable category, indicates little-to-no transfer of makeup onto the finger.

The third test, for Makeup Transfer Resistance Test was performed by preparing an in-vivo tape template and liquid foundation was applied and dried on the template for 10 minutes, as described above. The test composition was applied onto the foundation and allowed to dry for 5 minutes The template was then removed, leaving a 1.5 mm×1.5 mm square of foundation exposed to the test composition. A finger was then dragged once across the surface of the substrate with moderate pressure, and the drag pattern onto the skin was visually inspected and ranked 1-9. A "1," the most-desirable rating, indicates no drag pattern was observed. 2-4 indicate mild drag patterns. 5-7 indicate moderate drag patterns. 8-9 indicates very significant drag patterns.

The results are shown below.

| Ref. | Foam Quality | Makeup Removal During Application | Makeup Transfer Resistance |
| --- | --- | --- | --- |
| C1 | LOW | LOW | 6 |
| C2 | LOW | MED | 3 |
| C3 | LOW | HIGH | 3 |
| E1 | HIGH | LOW | 1 |
| E2 | HIGH | LOW | 2 |
| E3 | MEDIUM | LOW | 2 |

The results indicate that samples with water-soluble or dispersible polymer (E1, E2 and E3) perform well according to all three tests. Samples where water-soluble or dispersible polymer (C1, C2 and C3) is replaced with water or polymers that are not water-soluble/water-dispersible did not have desirable performance.

Example II—Surface Tension and Foam Collapse Rate

Twelve test compositions (B1-B12) or "concentrates" were prepared, eleven of which each had 2.5% by weight of various film-forming polymers and one had only water. Example B11 additionally included 0.52% aminomethylpropanol in order to neutralize the particular polymer. The various concentrates were evaluated for Surface Tension Value. The various concentrates were also filled into cans with propellant as described above and evaluated for Foam Collapse Rate.

Surface tension measurements were performed using Pendant Drop method described in this specification. Surface Tension Value. Foam collapse rate was performed using the Foam Collapse Rate Test as described in this specification. These results are shown in Table 2, below.

TABLE 2

| Reference | Polymer | Surface Tension (mN/m) | Foam Collapse Rate (mL/s) |
| --- | --- | --- | --- |
| B1 | None | 71.5 | Not Tested |
| B2 | POLYVINYLPYRROLLIDONE | 65.5 | 1.024 |
| B3 | POLYURETHANE-35 | 63.2 | 0.707 |
| B4 | POLYESTER-5 | 59.9 | 0.229 |
| B5 | POLYVINYLCAPROLACTAM | 56.6 | 0.243 |
| B6 | ACACIA SENEGAL GUM | 52.5 | 0.191 |
| B7 | VP/VA COPOLYMER | 49.1 | 0.843 |
| B8 | ACRYLATES COPOLYMER | 46.9 | 0.069 |
| B9 | POLYVINYL ALCOHOL | 44.2 | 0.011 |
| B10 | VP/ACRYLATES/LAURYL METHACRYLATE COPOLYMER | 41.1 | 0.018 |
| B11 | Octylacrylamide/acrylates/butylaminoethyl methacrylate[3] | 34.6 | 0.024 |
| B12 | AMP-ACRYLATES/ALLYL METHACRYLATE COPOLYMER | 34.3 | 0.009 |

The results above indicate that compositions with high surface tensions at the air liquid interface create foams that collapse fast. It is therefore desirable for compositions useful in the present invention to have Surface Tension Values to be less than about 63 mN/m, such as less than about 60 mN/m, such as less than about 44 mN/m, such as less than about 42 mN/m. It is also desirable, according to certain embodiments, for compositions useful in the present invention to have foam collapse rates that are less than about 0.7 ml/s such as less than about 0.3 ml/s, such as less than about 0.05 ml/s, such as less than about 0.025 ml/s, such as between about 0.005 ml/s and about 0.025 ml/s.

It will be apparent to those skilled in the art that various modifications and variations can be made in the compositions and methods according to the disclosure without departing from the spirit or scope of the disclosure. Thus, it is intended that the disclosure cover such modifications and variations and their equivalents.

The invention claimed is:

1. A method of treating keratinous substrates, comprising:
applying a makeup setting composition to a keratinous substrate having makeup formed thereon wherein the makeup setting composition comprises a gas phase dispersed in a condensed phase, wherein the condensed phase comprises a water-soluble or water-dispersible film former, and wherein the makeup setting composition is produced by actuating a packaged makeup setting product that includes a mousse-forming composition comprising the water-soluble or water-dispersible film former, wherein the mousse-forming composition comprises less than about 2% by weight of colorant.

2. The method of claim 1 further comprising shearing the makeup setting composition across the keratinous substrate having makeup formed thereon.

3. The method of claim 2 wherein the shearing comprises manually contacting the makeup setting composition to the keratinous substrate having makeup formed thereon and spreading the makeup setting composition across said keratinous substrate.

4. The method of claim 1, wherein the keratinous substrate is a user's skin.

5. The method of claim 1, wherein the mousse-forming composition has a Surface Tension Value of less than about 63 mN/m, wherein surface tension value is determined using a tensiometer standardized such that DI water has a surface tension value of 70-72 mN/m.

6. The method of claim 1, wherein the mousse-forming composition has a Surface Tension Value of less than about 60 mN/m, wherein surface tension value is determined using a tensiometer standardized such that DI water has a surface tension value of 70-72 mN/m.

7. The method of claim 1, wherein the mousse-forming composition has a Surface Tension Value of less than about 44 mN/m, wherein surface tension value is determined using a tensiometer standardized such that DI water has a surface tension value of 70-72 mN/m.

8. The method of claim 1, wherein the mousse-forming composition comprises from about 0.5% by weight to about 50% by weight of the water-soluble or water-dispersible film former.

9. The method of claim 1, wherein the mousse-forming composition comprises from about 40% to about 99% by weight of water.

10. The method of claim 1, wherein the mousse-forming composition is substantially free of film-formers that are neither water-soluble nor water-dispersible.

11. The method of claim 1, wherein the mouse-forming composition comprising about 0.5% by weight to about 20% by weight of the water-soluble or water-dispersible film former.

12. The method of claim 1, wherein the mousse-forming composition comprising about 0.5% by weight to about 10% by weight of the water-soluble or water-dispersible film former.

13. The method of claim 1, wherein the water-soluble or water-dispersible film former is a copolymer of octylacrylamide, acrylic acid, butylaminoethyl methacrylate, methyl methacrylate and hydroxypropyl methacrylate, AMP-acrylates/allyl methacrylate, polyvinylcaprolactam, or a combination thereof.

14. The method of claim 1, wherein the mousse-forming composition further comprises water and propellant.

15. The method of claim 1, wherein the mousse-forming composition is substantially free of surfactant.

16. The method of claim 14, wherein the mousse-forming composition is substantially free of surfactant.

17. The method of claim 1, wherein the mousse-forming composition comprises less than about 1% by weight of colorant.

18. The method of claim 1, wherein the mousse-forming composition comprises less than about 0.5% by weight of colorant.

19. The method of claim 1, wherein the mousse-forming composition comprises less than about 0.1% by weight of colorant.

* * * * *